US010604465B2

(12) United States Patent
Eijsbouts et al.

(10) Patent No.: US 10,604,465 B2
(45) Date of Patent: Mar. 31, 2020

(54) METHOD FOR MANUFACTURING OF BISPHENOL A

(71) Applicant: SABIC GLOBAL TECHNOLOGIES B.V., Bergen op Zoom (NL)

(72) Inventors: Paulus Johannes Maria Eijsbouts, Bergen op Zoom (NL); Rene Heinink, Bergen op Zoom (NL); Michel Mulder, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/462,374

(22) PCT Filed: Dec. 20, 2017

(86) PCT No.: PCT/IB2017/058231
§ 371 (c)(1),
(2) Date: May 20, 2019

(87) PCT Pub. No.: WO2018/116219
PCT Pub. Date: Jun. 28, 2018

(65) Prior Publication Data
US 2019/0270692 A1    Sep. 5, 2019

(30) Foreign Application Priority Data

Dec. 20, 2016  (EP) ..................... 16205247

(51) Int. Cl.
*C07C 37/20* (2006.01)
*C07C 37/84* (2006.01)

(52) U.S. Cl.
CPC .............. *C07C 37/84* (2013.01); *C07C 37/20* (2013.01); *C07C 2601/16* (2017.05)

(58) Field of Classification Search
CPC ................. C07C 37/20; C07C 37/84
See application file for complete search history.

(56) References Cited

U.S. PATENT DOCUMENTS

| 4,156,098 A | 5/1979 | Li |
| 4,294,993 A | 10/1981 | Li |
| 4,469,561 A | 9/1984 | Sikdar et al. |
| 4,492,807 A | 1/1985 | Aneja |
| 4,927,978 A | 5/1990 | Buechele et al. |
| 6,051,658 A | 4/2000 | Wehmeyer et al. |
| 6,875,986 B1 | 4/2005 | Yao et al. |
| 2003/0181768 A1 | 9/2003 | O'Young et al. |

FOREIGN PATENT DOCUMENTS

| GB | 1410750 A | 10/1975 |
| JP | 4067905 B2 | 3/2008 |
| JP | 2010150249 A | 7/2010 |
| SU | 798085 A1 | 1/1981 |

OTHER PUBLICATIONS

European Search Report for 16205247.6, filed Dec. 20, 2016, 4 pages.
International Search Report for International Application No. PCT/IB2017/058231, International filing date Dec. 20, 2017, dated Mar. 15, 2018, 6 pages.
Written Opinion for International Application No. PCT/IB2017/058231, International filing date Dec. 20, 2017, dated Mar. 15, 2018, 6 pages.

*Primary Examiner* — Sikarl A Witherspoon
(74) *Attorney, Agent, or Firm* — Cantor Colburn LLP

(57) ABSTRACT

The invention is directed to a method for manufacturing bisphenol A. The method for manufacturing bisphenol A comprises: a) reacting phenol and acetone in the presence of an acidic catalyst to form a reaction effluent, and b) crystallising p,p-bisphenol A from the reaction effluent so as to produce a crystal slurry, wherein reacting in step a) is performed in the presence of an inert co-solvent or wherein an inert co-solvent is added to the reaction effluent prior to crystallising in step b), and wherein the weight ratio between said inert co-solvent and said phenol during said crystallising is 60:40 or more.

19 Claims, 3 Drawing Sheets

METHOD FOR MANUFACTURING OF BISPHENOL A

CROSS REFERENCE TO RELATED APPLICATIONS

This application is a 371 of International Application No. PCT/IB2017/058231, filed Dec. 20, 2017, which is incorporated by reference in its entirety, and which claims priority to European Application Serial No. 16205247.6, filed Dec. 20, 2016.

The invention is directed to a method for manufacturing of bisphenol A. Bisphenol A (2,2'-bis(4-hydroxyphenyl) propane, also known as p,p-BPA) is predominantly used as an intermediate for the production of other products. The main uses of bisphenol A are binding, plasticising, and hardening functions in plastic products, paints/lacquers, binding materials and filler materials. The primary use for bisphenol A is in the production of polycarbonate resins, epoxy resins, unsaturated polyester, polysulphone, polyetherimide and polyarylate resins.

Bisphenol A is commercially prepared by condensing two moles of phenol with one mole of acetone in the presence of an acid catalyst as shown in equation (1) below.

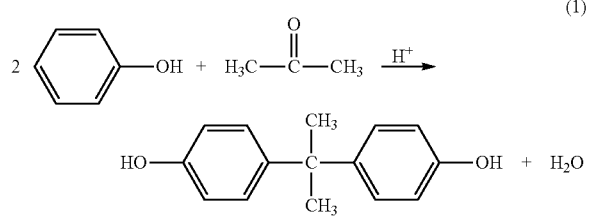

Typically, the phenol is present in the reaction in a molar excess of the stoichiometric requirement. It functions both as reactant and as solvent. In reaction, a part of the excess phenol is converted into bisphenol A, but the remaining excess of phenol is used as solvent for keeping all the bisphenol A isomers in solution. Therefore, it is possible to purify the bisphenol A direction from this reaction mixture, by cooling it down. This will initiate the crystallisation of pure p,p-BPA with only traces of the various by-products. However, since the thermodynamics dictate the formation of stable bisphenol A/phenol adduct crystals in a molar ratio of 1:1, the wet crystal mass obtained after washing of the mother liquor (i.e. the remaining liquid phase with all the by-products) with clean phenol, typically contains some 45% by total weight of the crystal mass of phenol. The thermodynamic bisphenol A/phenol phase diagram is shown in FIG. 1. In order to remove the phenol, a distillation and/or striping operation, preferably performed under vacuum is required to remove the excess of phenol. This is a very energy intensive process.

Commercial processes for purifying bisphenol A out of the reaction mixture of p,p-BPA with its various isomers and by-products use crystallisation as key process step. The mixture can be untreated reactor effluent, in which case excess phenol is present that acts as solvent, or the reaction effluent may be treated to remove excess water, acetone and phenol, in which case the mixture is concentrated in phenol or even phenol free. The crystallisation process can be done by cooling down the reactor effluent mixture resulting in a so-called bisphenol A/phenol adduct crystallisation process or the concentrated mixture may be diluted with a solvent at elevated temperature (solvents can be various aromatic, chlorinated alkanes, or simple alkanes). The low boiling solvent will bring evaporative cooling capability to the system. Due to the cooling process, possibly combined by solvent removal to increase the concentration, crystals are created that have a high concentration of the desired isomer, being the p,p-BPA isomer. The slurry is then filtered to remove the excess liquid and washed with clean solvent to obtain a cake (crystal mass) that is as free as possible of the liquid phase.

The commercial processes that use phenol as solvent, typically all commercial processes using an ion exchange resin as catalyst, are all hampered by the fact that the crystals that are formed are effectively bisphenol A/phenol adduct crystals with a molar ratio of 1:1 due to the fact that phenol is the main solvent. In essence the thermodynamics of the bisphenol A-phenol system dictates the formation of p,p-BPA/phenol adduct if the concentration of the starting solution is below 60% bisphenol A. The commercial processes remain well below this limit. The only commercial route around this has been to remove all phenol and purify the crude bisphenol A using solvent crystallisation processes. Consequently, these processes are thus very energy intensive.

U.S. Pat. No. 6,051,658 to Wehmeyer et al., is directed to catalyst useful for the condensation of an aldehyde or ketone. Disclosed is a process in which the product is precipitated in the reaction mixture is preferred for the preparation of bisphenol A, more particularly a process wherein the phenol:acetone feed contains from about 6:1 to about 15:1 molar ratios of phenol:acetone; the reaction mixture contains up to about 5% by weight of water to lower the freezing point of phenol; the catalyst is 3-mercaptopropanesulfonic or 4-mercaptobutanesulfonic acid in an amount from about 0.05 to about 0.50 equivalent per mole of acetone in the acetone:phenol feed; the reaction is carried out under ambient pressure; and the crystalline bisphenol A produced by the process is removed by filtration or centrifugation. Here, sufficient acetone is added and converted to initiate crystallization, but the crystals are essentially BPA:adducts. None of the examples create conditions that create pure p,p-BPA crystals in the solution.

US 2003/181768 to O'Young et al. discloses a system and method for producing bisphenol-A (BPA) wherein the phase equilibrium behaviour of a feed solution to a crystallizer is selectively controlled and adjusted to provide desired results. Bisphenol-A is produced from a reaction of phenol and acetone, forming a product solution including phenol, bisphenol-A, isomers of bisphenol-A, unreacted reactants and by-products. A solvent is used to selectively control the phase behaviour of the system. The solvents include water, alcohol, ketones, and acetone. Ketones create additional by-products in the reactor and need to be removed. Acetone will have to be removed or crystallization in the reactor will occur and plugging the catalyst system. Unfortunately water inhibits the reaction and will also require energy intensive removal, and alcohols can poison mercapto promoted catalyst systems. The process forms adducts which are removed using two crystallizers. The first crystallizer is an adduct crystallizer. The adduct crystals are separated off, remolten with added solvent at a temperature above 100° C. to obtain a homogenous mixture, and then recrystallized in a second crystallizer.

JP 2010/150249 to Asatani is directed to a method for making high purity bisphenol A. The method includes: a phase equilibrium behaviour of a three-component system comprising phenol with a specified process stream, bisphenol A, and a solvent (of 95 wt % acetone and 5 wt % water) is operated; substantially pure bisphenol A is recovered directly by crystallization from the solution; and the crystal purity if heightened by cleaning and recrystallization. The method fails to provide criterion on how to control the formation of the adduct vs. pure crystal formation.

GB 1410750A to Anton et al. is directed to a method for bisphenol production. Disclosed is a continuous process for the production of 2,2-bis-(4-hydroxyphenyl)-propane by the reaction of phenol with acetone in the presence of an acidic catalyst and ethyl mercaptan at a temperature of from 60 to 85° C., followed by removal of a light fraction from the reaction mixture by distillation and purification of the remaining reaction mixture.

Objective of the invention is to provide a method for manufacturing bisphenol A which overcomes one or more of the above discussed disadvantages of the prior art.

FIG. 5 illustrates that the selectivity will remain almost unchanged.

Figure 1:
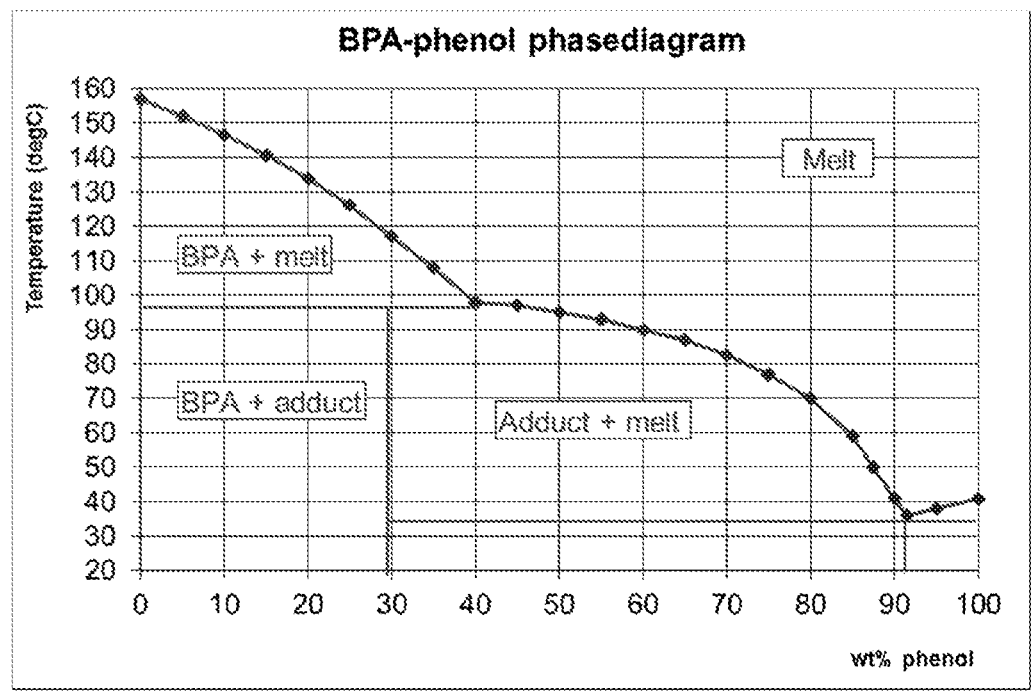
FIG. 1 is a thermodynamic bisphenol A/phenol phase diagram.

It was found that this objective can be met, at least in part, by using the phenol solvent in combination with a sufficient amount of inert co-solvent.

Accordingly, in a first aspect the invention is directed to a method for manufacturing bisphenol A comprising
   a) reacting phenol and acetone in the presence of an acidic catalyst to form a reaction effluent, and
   b) crystallising p,p-bisphenol A from the reaction effluent so as to produce a crystal slurry,
wherein reacting in step a) is performed in the presence of an inert co-solvent or wherein an inert co-solvent is added to the reaction effluent prior to crystallising in step b), and wherein the weight ratio between said inert co-solvent and said phenol during said crystallising is 60:40 or more.

Rather than forming bisphenol A/phenol adduct crystals from which phenol has to be removed, the method of the invention results in direct formation of p,p-BPA crystals. Since, the invention allows the formation of a crystal cake of pure p,p-bisphenol A and a low boiling point solvent, the final solvent removal can take place in smaller equipment (significantly less solvent to remove) and at lower temperatures giving less cause for thermal degradation of bisphenol A and thus improved product quality. Accordingly, the invention allows for a significant energy saving which is otherwise required for the removal of the excess phenol in order to obtain the p,p-BPA crystals. In other words, the present process does not require crystallization—re-melting—second crystallization, in order to attain the p,p-BPA crystals (e.g., having a purity of greater than or equal to 98% by weight). The present process can directly use the effluent of the reactor and avoid the formation of adduct.

In step a) phenol and acetone are reacted in the presence of an acidic catalyst to form a reaction effluent. In accordance with the invention, this reaction may be performed in the further presence of the inert co-solvent.

If the reaction is performed in the absence of inert co-solvent, then the molar ratio of phenol to acetone is preferably in the range of 3-30 moles of phenol per mole of acetone, and more preferably 5-15 moles of phenol per mole of acetone. If the reaction is performed in the presence of inert co-solvent, then the molar ratio of phenol to acetone is preferably in the range of 4-30 moles of phenol per mole of acetone, and more preferably 6-16 moles of phenol per mole of acetone. If the molar ratio of phenol to acetone is too small, then the reaction speed is likely to be too slow. If the molar ratio of phenol to acetone is too large, then the system becomes too dilute to have commercial significance.

The reaction temperature can be 40-150° C., preferably 60-110° C., more preferably 50-100° C. If the reaction temperature is lower than 40° C., not only the reaction speed is slow but also the reaction solution has a very high viscosity and may solidify. On the other hand, if the reaction temperature exceeds 150° C., it becomes difficult to control the reaction, and the selectivity of bisphenol A (p,p-BPA) is lowered. In addition, the catalyst may be decomposed or deteriorated.

The acidic catalyst can be a homogenous acidic catalyst or a solid acidic catalyst. In view of low corrosiveness of devices and easiness in separating the catalyst from the reaction mixture, solid acidic catalysts are preferred.

When a homogenous acidic catalyst is used, hydrochloric acid, sulphuric acid and the like are generally used. Hydrochloric acid is preferably used since it can be easily separated. When a solid acidic catalyst is used, a sulphonic acid-type ion-exchange resin is generally used. Examples thereof include sulphonated styrene-divinylbenzene copolymers, sulphonated cross-linked styrene polymers, phenol formaldehyde-sulphonic acid resins, and benzene formaldehyde-sulphonic acid resins. These catalysts may be used individually or in combination.

In accordance with the invention, the co-solvent is inert. In the context of this application, this is meant to indicate that the co-solvent does not participate in the reaction between phenol and acetone, and that it is stable in the presence of the catalyst system. The term co-solvent further implies that the co-solvent is other than phenol.

The inert co-solvent may suitably comprise one or more of an aromatic solvent, a $C_{1-9}$ alkane, and a chlorinated alkane. More preferably, the inert co-solvent comprises one or more selected from the group consisting of toluene, benzene, xylene, hexane, heptane, trichloro-ethylene, and dichloro-methylene. Even more preferably said inert co-solvent comprises or is toluene.

The inert co-solvent preferably has a boiling point of 125° C. or less, more preferably a boiling point of 120° C. or less, even more preferably a boiling point of 115° C. or less.

If the inert co-solvent is present during the reaction step a), then it is preferred that the weight ratio between the inert co-solvent and the phenol during the reaction step a) is 40:60 or more, such as in the range of from 40:60 to 80-20, preferably 50:50 or more, such as in the range of from 50:50 to 70:30. The weight ratio between the inert co-solvent and the phenol during the reaction step a) can be lower than the weight ratio between the inert co-solvent and the phenol during the crystallisation step b) because phenol will be converted into bisphenol A during the reaction, thereby increasing the toluene/phenol weight ratio.

The reaction of step a) may be performed batch-wise or continuously. Preferably, the reaction is performed in a fixed bed continuous reactor in which phenol and acetone are continuously fed into a reactor filled with an acid-type ion-exchange resin to react them. The reactor may be a single reactor, or maybe two or more reactors that are connected in series.

Optionally, the reaction mixture of step a) is subjected to a step for removing unreacted acetone, and water, e.g. by distillation. Such optional distillation may be performed under reduced pressure using a distillation column. In general such distillation is carried out at a pressure of 6.5-80 kPa and at a temperature of 70-180° C. Unreacted phenol then boils by azeotropy, and part thereof is removed.

Optionally, the bisphenol A may be concentrated by further removal of phenol. Such further distillation may typically be performed at 100-170° C. and a pressure of 5-70 kPa.

The reaction effluent obtained in step a) usually includes, in addition to bisphenol A, unreacted acetone, unreacted phenol, water produced during the reaction and other by-products.

If the reaction in step a) is performed in the presence of co-solvent, then the reaction effluent typically comprises
  10-50% by total weight of the reaction product of bisphenol A, preferably 16-35%, more preferably 20-35%.
  60-85% by total weight of the reaction product of phenol/co-solvent mixture, preferably 65-80%,
  0-5% by total weight of the reaction product of water, preferably 0-3%,
  0-5% by total weight of the reaction product of acetone, preferably 0-2%, and
  0-20% by total weight of the reaction product of by-products, typically 2-16%.

If the reaction in step a) is performed in the absence of co-solvent, then the reaction effluent typically comprises
  10-50% by total weight of the reaction product of bisphenol A, preferably 16-35%, more preferably 20-35%,
  60-85% by total weight of the reaction product of phenol, preferably 65-80%,
  0-5% by total weight of the reaction product of water, preferably 0-3%,
  0-3% by total weight of the reaction product of acetone, preferably 0-1.5%, and
  0-20% by total weight of the reaction product of by-products, typically 2-16%.

When the concentration of bisphenol A is more than 50% by total weight of the reaction product, the viscosity of the slurry becomes high, so that the transportation of the slurry becomes difficult. It is preferred that the reaction effluent comprises 16-35% by total weigh of the reaction effluent of bisphenol A, more preferably 20-35%. Such concentrations of bisphenol A in the reaction effluent may be achieved by using fresh phenol and acetone as feed for the reaction and by using a recycle stream with 10% by total weight of the recycle of bisphenol A. Such recycle stream may be derived from a step wherein the crystal slurry is subjected to a solid liquid separation step.

The one or more impurities that may be present in the reaction product obtained in step a) may include one or more selected from the group consisting of o,p-bisphenol A (2-(2-hydroxyphenyl)-2-(4-hydroxyphenyl)propane), BPX-1 (2,4-bis(α,α-dimethyl-4-hydroxybenzyl)phenol), Chr-1 (4'-hydroxyphenyl-2,2,4-trimethyl chroman, also known as chroman-1), Spi (2,2',3,3'-tetrahydro-1,1'-spirobi[indene], also known as spirobiindan), BPX-2 (4-(2-(4-(4-hydroxyphenyl)-2,2,4-trimethylchroman-6-yl)propan-2-yl)phenol), DMX (9,9-dimethylxanthene), 4-(4'-hydroxyphenyl)-2,2,4-trimethylchroman, and 2-(4'-hydroxyphenyl)-2,4,4-trimethylchroman.

The concentration of the total of these impurities in the reaction product obtained in step a) can be 5-15% by total weight of the reaction product, such as 6-12% by total weight of the phenol free reaction product or less, or 7-10% by total weight of the phenol free reaction product.

In a subsequent step, p,p-bisphenol A is crystallised from the reaction effluent so as to produce a crystal slurry. In accordance with the invention, the crystallisation step b) is performed in the presence of inert co-solvent which was either already present during the reaction step a) or is added after the reaction step a) and prior to the crystallisation step b).

The crystallisation step b) may be performed in a conventional manner by controlled cooling. Preferably, crystallisation is performed in a single step, thereby reducing operations costs. Single step crystallisation is preferred over multiple step crystallisation, although multiple step crystallisation is also possible, wherein the crystallisation comprises two or more steps in series.

The crystallising step can suitably be carried out at a temperature in the range of 40-70° C., preferably in the range of 45-65° C., more preferably in the range of 50-60° C.

The amount of inert co-solvent used in accordance with the method of the invention is such that during the step of crystallisation, the weight ratio between the inert co-solvent and the phenol is 60:40 or more. Preferably, the weight ratio between the inert co-solvent and the phenol during the step of crystallising is in the range of from 60:40 to 90:10. More preferably, the weight ratio between the inert co-solvent and the phenol during the step of crystallising is in the range of from 65:35 to 85:15. Even more preferably, the weight ratio between the inert co-solvent and the phenol during the step of crystallising is in the range of from 65:35 to 75:25

Typically, the mixture is cooled to a temperature of 40-70° C. so as to crystallise the bisphenol A to prepare a slurry. The cooling may, for instance, be carried out by means of an external heat exchanger or by a vacuum cooling crystallisation method in which the mixture is cooled down by evaporating the co-solvent using the vaporisation latent heat of the co-solvent under reduced pressure. A relatively high crystallisation temperature can result in higher purity, but the crystal yield will be lower. A relatively low crystallisation temperature can provide desirable yield but with lower purity. Preferably, the crystallisation temperature is in the range of 50-70° C.

Cooling may be performed in multiple subsequent cooling stages in order to achieve even higher purity. For example, a first cooling stage may be followed by a dwell time, after which a second cooling stage may be performed with an optional subsequent second dwell time and an optional subsequent third cooling stage.

The cooling may represent (or each of the cooling stages may independently represent) a cooling of the mixture with 5-40° C., such as 10-35° C., or 15-20° C., using a cooling rate of 0.1-1° C./min, such as 0.02-0.5° C./min. Each of the dwell times can last 20-120 minutes, such as 30-90 minutes. A smaller cooling rate can result in a higher purity product, but takes more time. Similarly, a longer dwell time can result in higher purity but takes more time.

Next, the crystal slurry containing the bisphenol A crystals can be separated into the bisphenol A crystals and the crystallisation mother liquid containing reaction by-products by conventional solid-liquid separation means, such as filtering and centrifugal separation. A part of the crystallisation mother liquid may be recycled in the reactor or to the crystallisation raw material. The solid-liquid separation produces a solid phase and a liquid phase.

Suitably, at least part of the liquid phase and/or the reaction effluent can be subjected to a water removal treatment, such as by distillation.

In a preferred embodiment, at least part of said liquid phase is recycled to the reacting in step a). This liquid phase recycle typically comprises unreacted phenol, a significant amount of toluene and dissolved p,p-bisphenol A, and almost all of the by-products. By recycling the by-products they may isomerise back into the p,p-bisphenol A form.

The solid phase is preferably washed with the inert co-solvent as used in the reaction. The p,p-bisphenol A crystals thus obtained can have a purity of 99.5% by weight or more, such as 99.7% by weight or more.

In an embodiment, the solid phase may be subjected to solvent stripping so as to obtain dry solid p,p-bisphenol A crystals.

Figure 2:
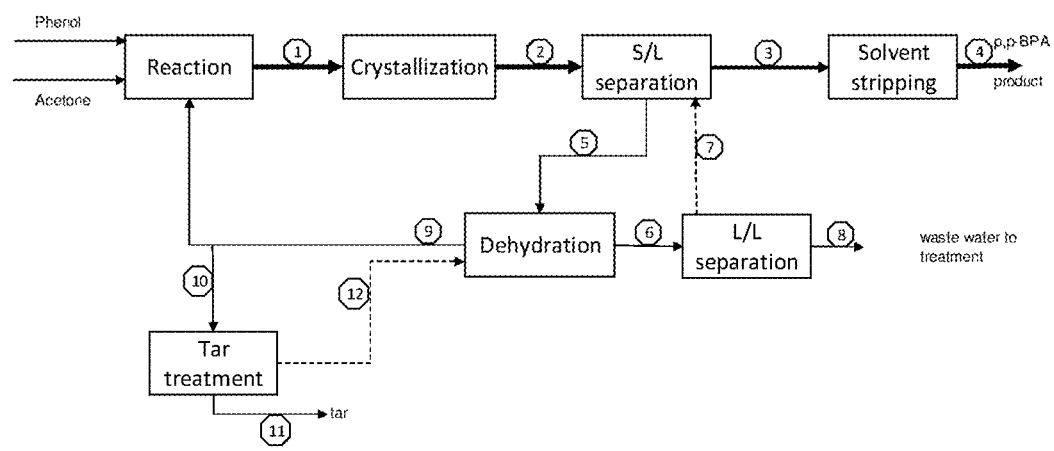
FIG. 2 is an embodiment of a process diagram for producing bisphenol A using a co-solvent system.

The method of the invention allows to define a new process for making bisphenol A using a co-solvent system that directly produces pure p,p-bisphenol A in crystallisation. This is illustrated in the process flow diagram of FIG. 2. The invention will now be further illustrated and described by means of the exemplary process diagram in FIG. 2. However, the invention is not limited to the embodiment described below.

Different co-solvents could be used, but toluene is of particular interest due to the characteristics of the ternary phase diagram of toluene-phenol-water. The process will therefore be explained hereinafter for toluene as co-solvent.

Fresh phenol and acetone are added to the reaction section with a dry mother liquor recycle stream (9). The reaction can be done in a packed bed reactor in a single stage, multiple stages using staged acetone addition, in down flow or up flow mode. It typically uses a sulphonated, cross-linked polystyrene catalyst as freely available in the market from a number of suppliers. The reaction may be promoted with a mercaptan either added in bulk or fixed to the catalyst backbone (ionically or covalently bound). The toluene/phenol ratio can be lower than the 60/40 target for crystallisation, because phenol will be converted into bisphenol A during the reaction, thereby increasing the toluene/phenol ratio. Typical reaction conditions will use 3-6% by total weight of the feed of acetone, operate with feed temperatures of 40-70° C., but more preferably 55-63° C. and feed rates varying from WHSV=0.3-4.0 h$^{-1}$. WHSV is defined as the feed rate (ton/h) divided by the amount of dry catalyst in the reactor (ton). The reaction effluent (1) will have an increased temperature against the feed due to the adiabatic nature of the packed bed reactors. The outlet temperature will depend on the actual inlet temperature as well as the amount of acetone converted.

The reaction effluent (1) is fed to the crystalliser(s). Crystallisation will occur upon cooling of the mixer and standard industry crystallisers can be used to accomplish this. Critical in this operation is that the toluene/phenol weight ratio exceeds the 60/40 ratio by weight in order to obtain pure p,p-bisphenol A crystals.

Depending on the exact composition the crystallisation temperature may be as high as 90° C., but typically above 70° C. Below this limit the whole mixture may solidify, making it impossible to process the crystal slurry (2).

Next, the crystal slurry (2) is separated in a solid-liquid separating unit and washed with toluene to remove various by-products and the excess phenol. The crystal mass (3) will mainly consist of pure p,p-bisphenol A crystals and 5-10% by weight of the total crystal mass of toluene. A small amount of by-products will either co-crystallise or remain in the cake due to less than 100% displacement wash. The solid-liquid separating unit can be any type of filter unit. Preferred are continuous drum filters, or a parallel assembly of discontinuous basket centrifuges. Depending on the type and operating conditions the toluene content in the cake will vary.

Next, the crystal mass (3) is fed to a solvent stripping operation. This can consist of a number of devices in series, e.g. a flash drum followed by a falling film evaporator, or a single unit. The main objective of this operation is to remove the solvent and obtain an essential solvent free molten bisphenol A product (4). A typical specification will be less than 100 ppm solvent. The solvent that is recovered can be routed to an intermediate storage tank, used as wash toluene in the filter operation, and can be used to keep the target solvent concentration in the crystallisation at the right target. Since toluene is the solvent to remove, temperatures in this operation do not need to exceed the melting temperature of bisphenol A significantly and can be limited to 165° C. The product can then be isolated as solid in e.g. a flaking or prilling operation or directly fed forward to downstream operation, e.g. an epoxy or polycarbonate production unit.

The liquid phase or mother liquor (5) from the solid-liquid separating unit is suitably treated in order to remove the excess of water, generated in the reaction, from the recycle stream. This is typically done in a distillation column. Since water and toluene form a low boiling point azeotrope at 85° C., the bottom temperature of this column does not need to exceed 110° C. and it could be operated at atmospheric pressures. The overhead of this dehydration column (6) will mainly consist of water, toluene and a small amount of phenol and unreacted acetone. Upon cooling to below 40° C., this mixture will phase separate into a toluene phase (7) (containing almost all organics) and a water phase (8) containing low enough amounts of organics that it can be send to a final treatment system prior to disposal of the waste water from the process. This dehydration process can also be done directly on the reaction effluent (1). Care should be taken in that process option, that the critical co-solvent/phenol weight ratio is observed prior to feeding the crystallisation operation.

The bottom stream of the dehydration column (9) contains the unreacted phenol, a significant amount of toluene and dissolved p,p-bisphenol A and almost all of the by-products. Most of this will be recycled back to the reactor in order to isomerise by-products back into the p,p-bisphenol A form. A small stream (10) will be purged to a tar treatment system. In this stream toluene and phenol are recovered and recycled back (12) to e.g. the feed of the dehydration column or used as cloth wash if used on the filter system. The bisphenol A stream can be further treated by cracking the bisphenol A with acid and/or caustic to break down the bisphenol A and recover more phenol out of this stream. Finally, a tar stream (11) is obtained which needs to be disposed of. Because it has a high caloric value, it can be used in a boiler system to generate steam.

This new process for making bisphenol A allows for significant energy savings. Less energy is required to melt the cake (max 10% solvent instead of 45% phenol). Less energy is required to evaporate the solvent in the stripping unit (or phenol desorption) (again max 10% instead of 45%).

Less energy is required to evaporate the solvent, because of the lower temperature requirements (165° C. against typically 210° C.). Less energy is required in the dehydration column, because of the low boiling water/toluene azeotrope (110° C. against 125° C.) and no vacuum operation is required.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include and intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by the following non-limiting examples.

EXAMPLES

Experimental work was done using a Lab Max™ system coupled with two probe based instruments: FBRM (Focused Beam Reflectance Measurement) and PVM (Particle Video Microscope) all supplied by Mettler Toledo™. The Lab Max™ system is further coupled with a lab scale pressure filter unit. The system consists of lab crystalliser with PVM and FBRM probe, Lab Max™ temperature controller, and filter unit.

The Lab Max is a fully automated, lab crystallisation temperature control unit. It is capable of controlling lab crystalliser temperature very accurately. It can follow programmed cooling and heating curves. The lab crystalliser is a jacketed glass vessel equipped with a stirrer. The stirrer speed is also controlled by the Lab Max™. The system is equipped with an automated dosing unit. This unit is used to add water or another chemical in different experiments.

FBRM is a laser based instrument. The probe is attached on the top of the crystalliser and reaches into the crystallising solution. Inside the probe is a laser light source. The laser light is sent through a rotational optic lens at the tip of the probe. In this way the laser beam scans through the solution in a circular motion. The linear velocity of the circulation is set to 2 m/s, and it can be adjusted. Once the beam crosses through the solid particle (or any other object, or example a bubble, which has different refractive index) the laser light is back scattered, and received by the sensors in the probe. In this way the probe is able to detect chord lengths of the crystals through which the beam scans.

The PVM is the second probe instrument, and it is also attached on the top of the crystalliser in similar fashion as FBRM. This probe also reaches into the solution, and it is capable of taking real time photos. The photos are of the dimensions of 800 with 1,000 micrometers.

Each of the FBRM, the Lab Max and the PVM are connected to a personal computer.

The lab crystalliser is a 2 litre jacketed glass vessel equipped with a pitched blade turbine stirrer. The temperature of the crystalliser is controlled by the Lab Max™ via heating oil. Lab Max™ temperature control can be programmed to follow different cooling or heating rates (° C./min), or different cooling or heating curves (second, third order curve, exponential curve, etc.). The stirrer speed is also controlled by the Lab Max™.

In order to filter the slurry after the crystallisation is complete a jacketed lab filtration unit from BHS Sonhofen™ is used. This allows for filtration temperatures to be the same as the end of the lab crystallisation protocol. A PEEK (polyether ether ketone) filter cloth is used in the filter and a small excess nitrogen pressure (0.05 barg) is applied to filter and wash the cake.

Feed mixtures were made using pure phenol, toluene and bisphenol A. At the start of the crystallisation experiment the mixture would be heated to a temperature that would ensure a homogeneous, clear solution.

The crystallisation protocol used in the examples was as follows: 380 g of the feed mixture was weighed in a 1 litre glass reactor at 90° C. First, the toluene and phenol were put in the reactor and next the solid bisphenol A in portions to aid dissolution, and the stirrer was set at 400 rpm. The mixture was stabilised at 90° C. for 30 minutes or at a higher temperature if needed to get a clear solution, and then cooled at a rate of 0.2° C./min. The temperature was kept constant for 30 minutes at nucleation temperature and this temperature was recorded. Then, the mixture was cooled approximately another 5° C. at a cooling rate of 0.2° C./min. The temperature was kept at that level during 10-20 minutes. Next, the slurry was samples and then the crystals were filtered and prepared for analysis. Crystal purity was determined by HPLC (high performance liquid chromatography) analysis on a phenol free basis.

The lab bisphenol A reactions were executed in small scale glass tube reactors (60 ml) in batch mode. The reaction temperature was controlled by placing the glass tube reactor into a heating block (AI), which was set at 70° C. The p,p-bisphenol A formation rate was followed by sampling small amounts (100 mg) from the mixture at different moments in time covering a total of 6 hours and analysing using HPLC analysis.

The chemicals used for the lab reactions were acetone, phenol, 3MPA (3-mercaptopropionic acid; co-promoter) and toluene as standard available lab chemicals. As catalyst a commercial catalyst of Lanxess™ was used: Lewatit™ K1131S.

First, the reactor was loaded with 1 g dried catalyst (catalyst is dried overnight in a vacuum oven at 95° C.) to remove any moisture. Next, phenol was added (10 g) to the catalyst and left overnight at 70° C. for the phenol and catalyst to arrive at a steady state phenol swollen condition. Then, the remainder of the phenol and toluene were added in the desired amounts. In a concentrated solution in phenol both acetone and the 3MPA co-promoter were added in such a way that the final starting concentration of 3MPA was 0.3 wt. % in the total mixture and acetone was 4 wt. %. The total mixture after adding all chemicals was 50 g. Samples for p,p-bisphenol A formation analysis were taken after 30 minutes, 1 hour, 2 hours, 3 hours, 4 hours, 5 hours, and 6 hours of the acetone/3MPA addition.

A number of crystallisation experiments were done with different mixtures of bisphenol A/phenol/toluene to identify at what ratio's of phenol/toluene the crystallisation experiment would generate p,p-bisphenol A crystals and at what temperature the crystallisation would start. In Table 1, "A" denotes bisphenol A/phenol adduct crystals and "P" denotes pure p,p-bisphenol A crystals.

TABLE 1

| Experiment | Composition | | | Crystallisation onset ° C. | Crystal type A or P | Full solidification ° C. |
|---|---|---|---|---|---|---|
| | BPA | phenol | toluene | | | |
| 1 | 30 | 20 | 50 | 82 (repeat 79) | P | 63 |
| 2 | 20 | 40 | 40 | 62 | A | 60 |
| 3 | 40 | 40 | 20 | 80 | A | 68 |
| 4 | 50 | 20 | 30 | 97 | P | 66 |
| 5 | 25 | 30 | 45 | 64 | A/P | 64 |
| From U.S. Pat. No. 4,294,993 | | | | Crystallisation temperature | | |
| 2 | 22 | 10 | 68 | 50 | P | Not observed |
| 3 | 14 | 6 | 80 | 50 | P | Not observed |
| 4 | 14 | 6 | 80 | 40.5 | P | Not observed |

The experiments of U.S. Pat. No. 4,294,993 are added because these also confirm the formation of pure p,p-bisphenol A crystals from a mixture with a ratio of co-solvent to phenol greater than 60/40 by weight. Although the starting material was an adduct crystal, that was re-dissolved the bisphenol A/phenol/toluene ratios used can be re-calculated. The cooling rate was 1° C. per 3.5 minutes of 0.29°/min. Cooling was done to a set temperature, which was possibly needed because of the low bisphenol A and high toluene content in these mixtures.

Experiments 4 and 5 are on the critical borderline. Based on the bisphenol A-phenol phase diagram a 50% bisphenol A solution would need to be prepared at around 100° C., as was required for experiment 4, and crystallisation would occur around 95° C. In this experiment it occurred at 97° C. Experiment 5 is different in the sense that the crystallisation onset and full solidification occurred at the same temperature. Apparently, that is the eutectic freezing point for the specific composition in the ternary phase diagram and indeed a mix of crystal types was found to exist.

Figure 3:
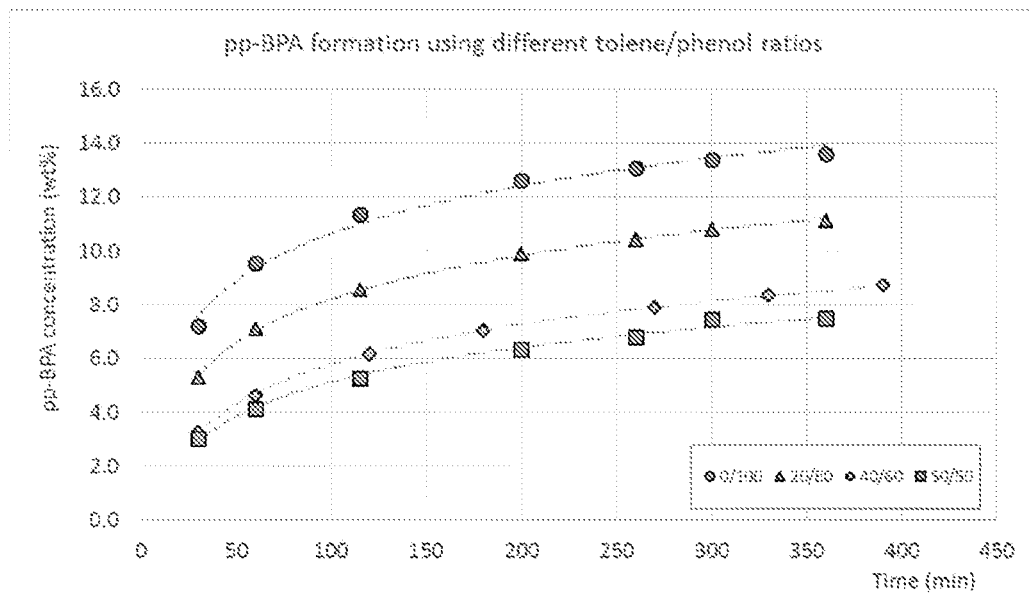
FIG. 3 is a graph representing p,p-bisphenol A (pp-BPA) formation in time in batch reaction experiments at different toluene/phenol ratio's (i.e., the toluene/phenol ratio entering the reactor). Illustrated is the reduction of conversion rate when adding toluene to the feed to the reactor (slowing it down almost linearly with the increase of the ratio).
Figure 4:
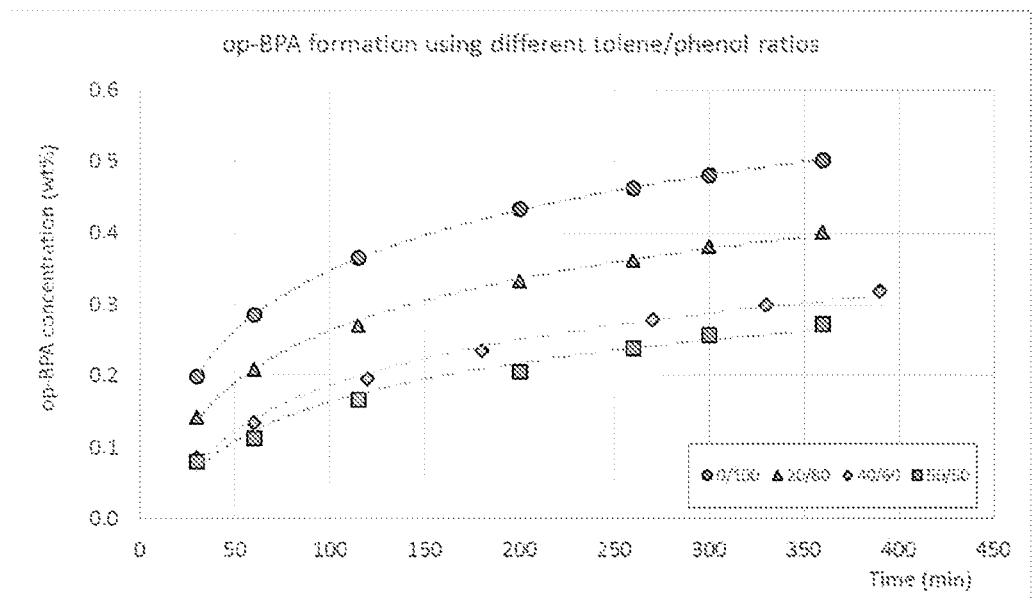
FIG. 4 is a graph representing o,p-bisphenol A (op-BPA) formation in time in batch reaction experiments at different toluene/phenol ratio's (i.e., the toluene/phenol ratio entering the reactor). Illustrated is the reduction of conversion rate when adding toluene to the feed to the reactor (slowing it down almost linearly with the increase of the ratio).
Figure 5:
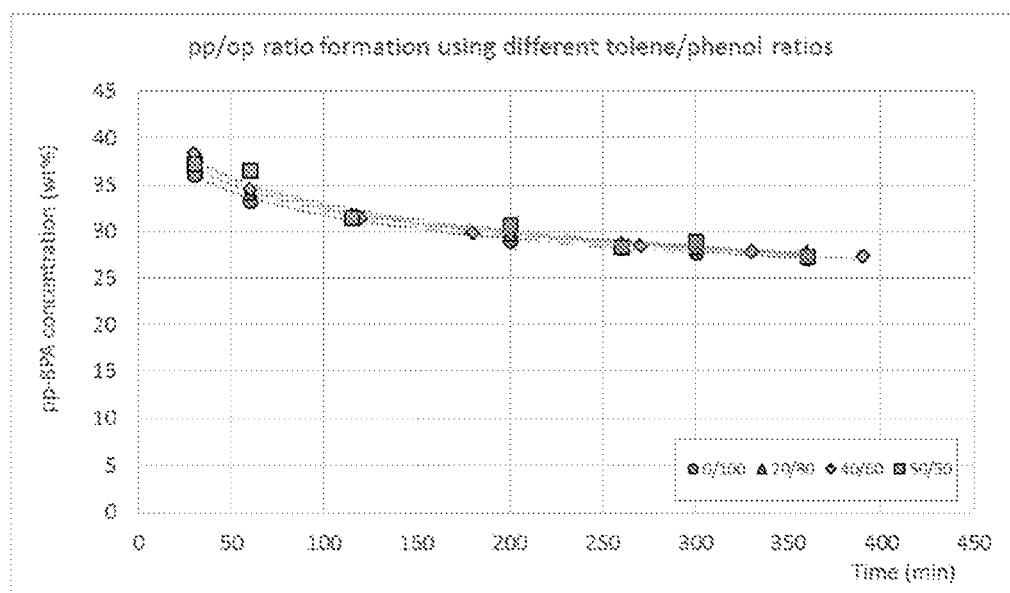
FIG. 5 is the p,p-BPA/o,p-BPA ratio derived from FIGS. 3 and 4, giving an indication of the overall p,p-BPA selectivity of the reaction at the different toluene/phenol ratios entering the reactor).

FIGS. 3-5 graphically illustrate BPA reaction experiments.

The lab BPA reactions were executed in small scale glass tube reactors (60 millilitre (ml)) in batch mode. The reaction temperature is controlled by placing the glass tube reactor into a heating block (AI), which was set at 70° C. The p,p-BPA formation rate was followed by sampling small amounts (100 milligrams (mg)) from the mixture at different moments in time covering a total of 6 hours and analysing using HPLC analysis (High Pressure Liquid Chromatography).

The chemicals used for the lab reactions were acetone, phenol, 3-mercaptopropionic acid (3MPA; co-promoter) and toluene. As catalyst a commercial catalyst of Lanxess™ was used: Lewatit™ K1131S The reaction protocol was as follows: First the reactor is loaded with 1 g dried catalyst (catalyst is dried overnight in a vacuum oven at 95° C.) to remove any moisture. Next phenol is added (10 g) to the catalyst and left overnight at 70° C. for the phenol and catalyst to arrive at a steady state phenol swollen condition. Then the remainder of the phenol and toluene were added in the desired amounts. In a concentrated solution in phenol both acetone and the 3-MPA co-promoter were added in such a way that the final starting concentration of 3-MPA was 0.3 wt. % in the total mixture and acetone was 4 wt. %. The total mixture after adding all chemicals was 50 g. Samples for p,p-BPA formation analysis were taken after 30 min, 1 hour (hr), 2 hr, 3 hr, 4 hr, 5 hr, and 6 hours of the acetone/3-MPA addition. As noted above, the results are illustrated in FIGS. 3-5.

Set forth below are some aspects of the method disclosed herein.

Aspect 1: A method for manufacturing bisphenol A, comprising: a) reacting phenol and acetone in the presence of an acidic catalyst to form a reaction effluent, and b) crystallising p,p-bisphenol A from the reaction effluent so as to produce a crystal slurry, preferably in a single crystallizer, wherein reacting in step a) is performed in the presence of an inert co-solvent or wherein an inert co-solvent is added to the reaction effluent prior to crystallising in step b), and wherein the weight ratio between said inert co-solvent and said phenol during said crystallising is 60:40 or more.

Aspect 2: The method according to claim 1, wherein the weight ratio between said inert co-solvent and said phenol during said crystallising is in the range of from 60:40 to 90:10, preferably in the range of from 65:35 to 85:15, more preferably in the range of from 65:35 to 75:25.

Aspect 3: The method according to Aspect 1 or 2, wherein said inert co-solvent has a boiling point of 125° C. or less, preferably a boiling point of 120° C. or less, more preferably a boiling point of 115° C. or less.

Aspect 4: The method according to any one of Aspects 1-3, wherein said inert co-solvent comprises one or more of an aromatic solvent, a $C_{1-9}$ alkane, and a chlorinated alkane; preferably said inert co-solvent comprises a chlorinated alkane.

Aspect 5: The method according to any one of Aspects 1-4, wherein said inert co-solvent comprises one or more selected from the group consisting of toluene, benzene, xylene, hexane, heptane, trichloro-ethylene, and trichloromethylene, preferably said inert co-solvent is toluene.

Aspect 6: The method according to any one of Aspects 1-5, wherein said reaction effluent comprises 16-35% by total weight of the reaction effluent of bisphenol A, preferably said reaction effluent comprises 20-35% by total weight of the reaction effluent of bisphenol A.

Aspect 7: The method according to any one of Aspects 1-6, wherein said method further comprises separating the crystal slurry in a solid-liquid separating unit, such as a filter unit, to produce a solid phase and a liquid phase.

Aspect 8: The method according to Aspect 7, wherein at least part of said liquid phase and/or said reaction effluent is subjected to a water removal treatment, such as by distillation.

Aspect 9: The method according to Aspect 7 or 8, wherein at least part of said liquid phase is recycled to the reacting in step a).

Aspect 10: The method according to any one of Aspects 7-9, wherein said solid phase is washed with inert co-solvent.

Aspect 11: The method according to any one of Aspects 7-10, wherein said solid phase is subjected to solvent stripping.

Aspect 12: The method according to any one of Aspects 1-11, wherein said crystallising comprises cooling of at least part of the reaction effluent.

Aspect 13: The method according to any one of Aspects 1-12, wherein said reacting is performed in the presence of inert co-solvent and wherein the weight ratio between said inert co-solvent and said phenol during said reacting is 50:50 or more.

Aspect 14: The method according to any one of Aspects 1-13, wherein said crystallising is performed at a temperature of 70° C. or more, preferably 80° C. or more.

Aspect 15: The method according to any one of Aspects 1-14, wherein said inert co-solvent does not participate in the reaction; and preferably the inert co-solvent does not poison the catalyst.

Aspect 16: The method according to any one of Aspects 1-15, wherein the catalyst comprises mercaptan, preferably the mercaptan is in bulk, or more preferably the mercaptan is fixed to the catalyst backbone.

Aspect 17: The method according to any one of Aspects 1-16, wherein the p,p-bisphenol A crystals have a purity of 99.5% by weight or more, preferably a purity of 99.7% by weight or more.

Aspect 18: The method according to any one of Aspects 1-17, wherein the p,p-bisphenol A crystals have a purity of 99.5% by weight or more, after a single crystallization, preferably without re-melting.

Aspect 19: The method according to any one of Aspects 1-18, wherein the reaction effluent is directly crystallized wherein the weight ratio between said inert co-solvent and said phenol during this crystallising is 60:40 or more.

Aspect 20: The method according to any one of Aspects 1-18, wherein the reaction effluent is crystallized without re-melting before the crystallization.

The invention claimed is:

1. A method for manufacturing bisphenol A, comprising:
    a) reacting phenol and acetone in the presence of an acidic catalyst to form a reaction effluent, and
    b) crystallising p,p-bisphenol A from the reaction effluent so as to produce a crystal slurry;
    wherein reacting in step a) is performed in the presence of an inert co-solvent or wherein an inert co-solvent is added to the reaction effluent prior to crystallising in step b); and
    wherein the weight ratio between said inert co-solvent and said phenol during said crystallising is 60:40 or more.

2. The method according to claim 1, wherein the weight ratio between said inert co-solvent and said phenol during said crystallising is in the range of from 60:40 to 90:10.

3. The method according to claim 1, wherein said inert co-solvent has a boiling point of 125° C. or less.

4. The method according to claim 1, wherein said inert co-solvent comprises one or more of an aromatic solvent, a $C_{1-9}$ alkane, and a chlorinated alkane.

5. The method according to claim 1, wherein said inert co-solvent comprises one or more selected from the group consisting of toluene, benzene, xylene, hexane, heptane, trichloro-ethylene, and trichloro-methylene.

6. The method according to claim 1, wherein said reaction effluent comprises 16-35% by total weight of the reaction effluent of bisphenol A by total weight of the reaction effluent of bisphenol A.

7. The method according to claim 1, wherein said method further comprises separating the crystal slurry in a solid-liquid separating unit, such as a filter unit, to produce a solid phase and a liquid phase.

8. The method according to claim 7, wherein at least part of said liquid phase and/or said reaction effluent is subjected to a water removal treatment.

9. The method according to claim 7, wherein at least part of said liquid phase is recycled to the reacting in step a).

10. The method according to claim 7, wherein said solid phase is washed with inert co-solvent.

11. The method according to claim 7, wherein said solid phase is subjected to solvent stripping.

12. The method according to claim 1, wherein said crystallising comprises cooling of at least part of the reaction effluent.

13. The method according to claim 1, wherein said reacting is performed in the presence of inert co-solvent and wherein the weight ratio between said inert co-solvent and said phenol during said reacting is 50:50 or more.

14. The method according to claim 1, wherein said crystallising is performed at a temperature of 70° C. or more.

15. The method according to claim 1, wherein the p,p-bisphenol A crystals have a purity of 99.5% by weight or more after a single crystallization.

16. The method according to claim 1,
    wherein the weight ratio between said inert co-solvent and said phenol during said crystallising is in the range of from 65:35 to 75:25;
    wherein said inert co-solvent has a boiling point of 120° C. or less;
    wherein said inert co-solvent comprises one or more of an aromatic solvent, a $C_{1-9}$ alkane, and a chlorinated alkane;
    wherein said inert co-solvent is toluene;
    wherein said reaction effluent comprises 20-35% by total weight of the reaction effluent of bisphenol A; and
    wherein said crystallising is performed at a temperature of 80° C. or more.

17. The method according to claim 16, wherein said method further comprises separating the crystal slurry in a solid-liquid separating unit, and wherein at least part of said liquid phase and/or said reaction effluent is subjected to a water removal treatment, such as by distillation.

18. The method according to claim 17, wherein at least part of said liquid phase is recycled to the reacting in step a).

19. The method according to claim 16, wherein the p,p-bisphenol A crystals have a purity of 99.5% by weight or more after a single crystallization.

* * * * *